(12) United States Patent
Guo et al.

(10) Patent No.: US 10,086,105 B2
(45) Date of Patent: Oct. 2, 2018

(54) CHITOSAN FOAM MEDICAL DEVICES AND METHODS

(71) Applicant: Providence Health System—Oregon, Portland, OR (US)

(72) Inventors: Jian Xin Guo, Portland, OR (US); Kenton W. Gregory, Portland, OR (US)

(73) Assignee: Providence Health System—Oregon, Portland, OR (US)

( * ) Notice: Subject to any disclaimer, the term of this patent is extended or adjusted under 35 U.S.C. 154(b) by 0 days.

(21) Appl. No.: 14/847,526

(22) Filed: Sep. 8, 2015

(65) Prior Publication Data

US 2015/0374877 A1 Dec. 31, 2015

Related U.S. Application Data

(62) Division of application No. 13/122,723, filed as application No. PCT/US2009/059726 on Oct. 6, 2009, now abandoned.

(60) Provisional application No. 61/103,067, filed on Oct. 6, 2008.

(51) Int. Cl.
| | |
|---|---|
| *A61L 15/28* | (2006.01) |
| *A61F 13/15* | (2006.01) |
| *A61L 15/42* | (2006.01) |
| *A61L 15/44* | (2006.01) |
| *B29C 44/00* | (2006.01) |
| *A61F 13/00* | (2006.01) |
| *B29K 105/04* | (2006.01) |
| *B29L 31/00* | (2006.01) |

(52) U.S. Cl.
CPC ........ *A61L 15/28* (2013.01); *A61F 13/00012* (2013.01); *A61F 13/00063* (2013.01); *A61F 13/00987* (2013.01); *A61F 13/00991* (2013.01); *A61F 13/15577* (2013.01); *A61L 15/425* (2013.01); *A61L 15/44* (2013.01); *B29C 44/005* (2013.01); *A61F 2013/0054* (2013.01); *A61F 2013/0071* (2013.01); *A61F 2013/0074* (2013.01); *A61F 2013/0091* (2013.01); *A61F 2013/00106* (2013.01); *A61F 2013/00314* (2013.01); *A61F 2013/00472* (2013.01); *A61F 2013/00719* (2013.01); *A61F 2013/00757* (2013.01); *A61F 2013/00931* (2013.01); *A61L 2300/404* (2013.01); *A61L 2300/408* (2013.01); *A61L 2300/412* (2013.01); *A61L 2300/418* (2013.01); *A61L 2400/04* (2013.01); *A61L 2430/34* (2013.01); *B29K 2005/00* (2013.01); *B29K 2105/045* (2013.01); *B29K 2995/0037* (2013.01); *B29L 2031/753* (2013.01)

(58) Field of Classification Search
CPC .......... A61F 13/00012; A61F 13/00987; A61F 13/00991; A61F 13/00063; A61F 13/15577; A61F 2013/00106; A61F 2013/00314; A61F 2013/00472; A61F 2013/0054; A61F 2013/0071; A61F 2013/00719; A61F 2013/0074; A61F 2013/00757; A61F 2013/0091; A61F 2013/00931; A61L 15/28; A61L 15/425; A61L 15/44; A61L 2300/408; A61L 2400/04; A61L 2430/34; A61L 2300/418; A61L 2300/412; A61L 2300/404; B29C 44/005; C08L 5/08; B29K 2105/045; B29K 2005/00; B29K 2995/0037; B29L 2031/753

See application file for complete search history.

(56) References Cited

U.S. PATENT DOCUMENTS

| | | | |
|---|---|---|---|
| 2,610,625 | A | 9/1952 | Sifferd et al. |
| 2,858,830 | A | 11/1958 | Robins |
| 2,923,664 | A | 2/1960 | Cook et al. |
| 3,551,556 | A | 12/1970 | Kliment et al. |
| 3,632,754 | A | 1/1972 | Balassa |
| 3,800,792 | A | 4/1974 | Russell |
| 3,849,238 | A | 11/1974 | Gould et al. |
| 3,902,497 | A | 9/1975 | Casey |
| 3,911,116 | A | 10/1975 | Balassa |
| 3,954,493 | A | 5/1976 | Battista et al. |
| 3,977,406 | A | 8/1976 | Roth |
| 4,040,884 | A | 8/1977 | Roth |
| 4,056,103 | A | 11/1977 | Kaczmarzyk et al. |
| 4,068,757 | A | 1/1978 | Casey |
| 4,094,743 | A | 6/1978 | Leuba |
| 4,195,175 | A | 3/1980 | Penniston et al. |
| 4,292,972 | A | 10/1981 | Palwelchak et al. |
| 4,373,519 | A | 2/1983 | Errede et al. |
| 4,394,373 | A | 7/1983 | Malette et al. |
| 4,452,785 | A | 6/1984 | Malette et al. |
| 4,460,642 | A | 7/1984 | Errede et al. |
| 4,501,835 | A | 2/1985 | Berke |

(Continued)

FOREIGN PATENT DOCUMENTS

| | | |
|---|---|---|
| EP | 0353972 | 2/1990 |
| EP | 0477979 | 9/1991 |

(Continued)

OTHER PUBLICATIONS

Allan et al., "Biomedical Applications of Chitin and Chitosan." Chitin, Chitosan, and Related Enzymes—Accademic Press, Inc.: 119-133, 1984.

(Continued)

*Primary Examiner* — Doan T Phan
(74) *Attorney, Agent, or Firm* — Seed IP Law Group LLP

(57) ABSTRACT

The invention provides a solid foam wound dressing useful for hemorrhage control and wound repair, as well as methods for making such a wound dressing.

22 Claims, 6 Drawing Sheets

(56) References Cited

U.S. PATENT DOCUMENTS

| | | |
|---|---|---|
| 4,524,064 A | 6/1985 | Nambu |
| 4,532,134 A | 7/1985 | Malette et al. |
| 4,533,326 A | 8/1985 | Anthony |
| 4,541,426 A | 9/1985 | Webster |
| 4,599,209 A | 7/1986 | Dautzenberg et al. |
| 4,651,725 A | 3/1987 | Kifune et al. |
| 4,684,370 A | 8/1987 | Barrett |
| 4,699,135 A | 10/1987 | Motosugi et al. |
| 4,772,419 A | 5/1988 | Malson et al. |
| 4,759,348 A | 7/1988 | Cawood |
| 4,833,237 A | 5/1989 | Kawamura et al. |
| 4,882,162 A | 11/1989 | Ikada et al. |
| 4,948,540 A | 8/1990 | Nigam |
| 4,952,618 A | 8/1990 | Olsen |
| 4,956,350 A | 9/1990 | Mosbey |
| 4,958,011 A | 9/1990 | Bade |
| 4,960,413 A | 10/1990 | Sagar et al. |
| 4,973,493 A | 11/1990 | Guire |
| 4,977,892 A | 12/1990 | Ewall |
| 5,006,071 A | 6/1991 | Carter |
| 5,024,841 A | 6/1991 | Chu et al. |
| 5,035,893 A | 7/1991 | Shioya et al. |
| 5,062,418 A | 11/1991 | Dyer et al. |
| 5,110,604 A | 5/1992 | Miyata et al. |
| 5,154,928 A | 10/1992 | Andrews |
| 5,206,028 A | 4/1993 | Li |
| 5,254,301 A | 10/1993 | Sessions et al. |
| 5,300,494 A | 4/1994 | Brode, II et al. |
| 5,376,376 A | 12/1994 | Li |
| 5,378,472 A | 1/1995 | Muzzarelli |
| 5,420,197 A | 5/1995 | Lorenz et al. |
| 5,454,719 A | 10/1995 | Hamblen |
| 5,525,710 A | 6/1996 | Unger et al. |
| 5,571,181 A | 11/1996 | Li |
| 5,597,581 A | 1/1997 | Kaessmann et al. |
| 5,643,596 A | 7/1997 | Pruss et al. |
| 5,700,476 A | 12/1997 | Rosenthal et al. |
| 5,738,860 A | 4/1998 | Sch et al. |
| 5,756,111 A | 5/1998 | Yoshikawa et al. |
| 5,765,682 A | 6/1998 | Bley et al. |
| 5,797,960 A | 8/1998 | Stevens et al. |
| 5,821,271 A | 10/1998 | Roenigk |
| 5,827,265 A | 10/1998 | Glinsky et al. |
| 5,836,970 A | 11/1998 | Pandit |
| 5,840,777 A | 11/1998 | Eagles et al. |
| 5,858,292 A | 1/1999 | Dragoo et al. |
| 5,858,350 A | 1/1999 | Vournakis et al. |
| 5,952,618 A | 9/1999 | Deslauriers |
| 5,961,478 A | 10/1999 | Timmermans |
| 6,042,877 A | 3/2000 | Lyon et al. |
| 6,054,122 A | 4/2000 | MacPhee et al. |
| 6,103,369 A | 8/2000 | Lucast et al. |
| 6,124,273 A | 9/2000 | Drohan et al. |
| 6,156,330 A | 12/2000 | Tsukada et al. |
| 6,162,241 A | 12/2000 | Coury et al. |
| 6,225,521 B1 | 5/2001 | Gueret |
| 6,270,515 B1 | 8/2001 | Linden et al. |
| 6,406,712 B1 | 6/2002 | Rolf |
| 6,448,462 B2 | 9/2002 | Groitzsch et al. |
| 6,454,787 B1 | 9/2002 | Maddalo et al. |
| 6,485,667 B1 | 11/2002 | Tan |
| 6,486,285 B2 | 11/2002 | Fujita |
| 6,548,081 B2 | 4/2003 | Sadozai et al. |
| 6,548,569 B1 | 4/2003 | Williams et al. |
| 6,552,244 B1 | 4/2003 | Jacques et al. |
| 6,565,878 B2 | 5/2003 | Schoenfedit et al. |
| 6,566,577 B1 | 5/2003 | Addison et al. |
| 6,599,891 B2 | 7/2003 | North et al. |
| 6,693,180 B2 | 2/2004 | Lee et al. |
| 6,726,712 B1 | 4/2004 | Raeder-Devens et al. |
| 6,750,262 B1 | 6/2004 | Hahnle et al. |
| 6,855,860 B2 | 2/2005 | Ruszczak et al. |
| 6,863,924 B2 | 3/2005 | Ranganathan et al. |
| 6,864,245 B2 | 3/2005 | Vournakis et al. |
| 6,992,233 B2 | 1/2006 | Drake et al. |
| 7,019,191 B2 | 3/2006 | Looney et al. |
| 7,371,403 B2 | 5/2008 | McCarhty et al. |
| 7,402,172 B2 | 7/2008 | Chin et al. |
| 7,482,503 B2 | 1/2009 | Gregory et al. |
| 7,546,812 B2 | 6/2009 | Eastin et al. |
| 7,637,934 B2 | 12/2009 | Mangiardi et al. |
| 7,820,872 B2 | 10/2010 | Gregory et al. |
| 7,850,709 B2 | 12/2010 | Cummins et al. |
| 7,897,832 B2 | 3/2011 | McAdams et al. |
| 8,063,265 B2 | 11/2011 | Beck et al. |
| 2001/0045177 A1 | 11/2001 | Harvey et al. |
| 2002/0035391 A1 | 3/2002 | Mikus et al. |
| 2002/0161375 A1 | 10/2002 | Barry et al. |
| 2005/0036955 A1 | 2/2005 | DeGould |
| 2005/0123581 A1 | 6/2005 | Ringeisen et al. |
| 2005/0137512 A1 | 6/2005 | Campbell et al. |
| 2005/0143817 A1 | 6/2005 | Hunter et al. |
| 2005/0147656 A1 | 7/2005 | McCarthy et al. |
| 2005/0240137 A1 | 10/2005 | Zhu et al. |
| 2006/0004314 A1 | 1/2006 | McCarthy et al. |
| 2006/0008419 A1 | 1/2006 | Hissink et al. |
| 2006/0083710 A1 | 4/2006 | Joerger et al. |
| 2006/0184224 A1 | 8/2006 | Angel |
| 2006/0211973 A1 | 9/2006 | Gregory et al. |
| 2007/0009578 A1* | 1/2007 | Moller ............... A61L 15/28 424/443 |
| 2007/0021703 A1* | 1/2007 | McCarthy ............ A61L 15/28 602/43 |
| 2007/0066694 A1 | 3/2007 | Gaserod et al. |
| 2007/0066920 A1 | 3/2007 | Hopman et al. |
| 2007/0083137 A1 | 4/2007 | Hopman et al. |
| 2007/0237811 A1 | 10/2007 | Scherr |
| 2007/0255194 A1 | 11/2007 | Gudnason et al. |
| 2007/0255243 A1 | 11/2007 | Kaun et al. |
| 2007/0276308 A1 | 11/2007 | Huey et al. |
| 2008/0132990 A1 | 6/2008 | Richardson |
| 2008/0147019 A1 | 6/2008 | Song et al. |
| 2008/0213344 A1* | 9/2008 | McCarthy ......... A61F 13/0203 424/445 |
| 2008/0241229 A1 | 10/2008 | Li et al. |

FOREIGN PATENT DOCUMENTS

| | | |
|---|---|---|
| EP | 0643963 | 3/1995 |
| EP | 1462123 | 9/2004 |
| JP | 60-142927 | 7/1985 |
| JP | 62-039506 | 2/1987 |
| JP | 63-090507 | 8/1988 |
| JP | 07-116241 | 5/1995 |
| JP | 11-342153 | 12/1999 |
| JP | 2002-233542 | 8/2002 |
| WO | WO 98/48861 | 11/1989 |
| WO | WO 95/05794 | 3/1995 |
| WO | WO 99/02587 | 1/1999 |
| WO | WO 00/56256 | 9/2000 |
| WO | WO 02/102276 | 12/2002 |
| WO | WO 03/47643 | 6/2003 |
| WO | WO 03/79946 | 10/2003 |
| WO | WO 03/92756 | 11/2003 |
| WO | WO 03/101310 | 12/2003 |
| WO | WO 04/47695 | 6/2004 |
| WO | WO 04/60412 | 7/2004 |
| WO | WO 05/62880 | 7/2005 |
| WO | WO 06/49463 | 5/2006 |
| WO | WO 06/071649 | 7/2006 |
| WO | WO 06/079822 | 8/2006 |
| WO | WO 07/09050 | 1/2007 |
| WO | WO 07/056066 | 5/2007 |
| WO | WO 07/74327 | 7/2007 |
| WO | WO 08/33462 | 3/2008 |
| WO | WO 08/36225 | 3/2008 |

OTHER PUBLICATIONS

Anema et al., "Potential Uses of Absorbable Fibrin Adhesive Bandage for Genitourinary Trauma." World Journal of Surgery, vol. 25: 1573-1577, 2001.

(56) References Cited

OTHER PUBLICATIONS

Bégin et al., "Antimicrobial films produced from chitosan." International Journal of Biological Macromolecules, vol. 26: 63-67, 1999.
Belman et al., "From the Battlefield to the Steet." Per declaration submitted in U.S. Appl. No. 10/480,827, dated Dec. 17, 2007, poster presentation was made at the ATACCC Conference, Aug. 2006.
Bendix., "Chemical synthesis of polyactide and its copolymers for medical applications." Polymer Degradation and Stability, vol. 59: 129-135, 1998.
Chan et al., "Comparision of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage." The Journal of Trauma: 454-458, 2000.
CNN Transcript—3pp., Jun. 8, 2006.
Cole et al., "A pilot study evaluating the efficacy of a fully acetylated poly-N-acetyl glucosamine membrane formulation as a topical hemostatic agent" Surgery, vol. 126, No. 3: 510-517, 1999.
HemCon Manufacturing Materials. Per declaration submitted in U.S. Appl. No. 10/480,827, dated Dec. 17, 2007, materials were submitted as supporting evidence for declaration.
Horesh et al., "Pre-hospital use of the HemCon bandage." Per declaration submitted in U.S. Appl. No. 10/480,827, dated Dec. 17, 2007, poster presentation was made at the WCDEM Conference, May 2007.
Kiley, Kevin, "Department of the Army memo." Jul. 20, 2005.
Kumar, Ravi, "Chitin and chitosan fibres: A review." Bulletin of Material Science: vol. 22, No. 5: 905-915, Aug. 1999.
Luo et al., "The role of poly(ethylene glycol) in the formation of silver nanoparticles." Journal of Colloid and Interface Science, vol. 288: 444-448, 2005.
Malette et al., "Chitosan: A New Hemostatic." The Annals of Thoratic Surgery, vol. 36, No. 1: 55-58, Jul. 1983.
Martin et al., "Medical applications of poly-4-hydroxybutyrate: a strong flexible absorbable biomaterial." Biochemical Engineering Journal, vol. 16: 97-105, 2003.
Mi et al., "Fabrication and characterization of a sponge-like asymmetric chitosan membrane as a wound dressing." Biomaterials, vol. 22: 165-173, 2001.
Moody, Robin J., "HemCon bandage stakes claim to soldier's kit bag" Portland Business Journal, Nov. 4, 2005.
Ohshima et al., "Clinical Application of Chitin Non-Woven Fabric as Wound Dressing." European Journal of Plastic Surgery, vol. 10: 66-69, 1987.
Ohshima et al., "Clinical application of new chitin non-woven fabric and new chitin sponge sheet as wound dressing." European Journal of Plastic Surgery, vol. 14: 207-211, 1991.
Olsen et al., "Biomedical Applications of Chitin and its Derivatives." Chitin and Chitosan: Proceedings from the 4th International Conference on Chitin and Chitosan, 813-829, 1988.
Park et al., "Platelet derived growth factor releasing chitosan sponge for periodontal bone regeneration." Biomaterials, vol. 21: 153-159, 2000.
Percot et al., "Optimization of Chitin Extraction from Shrimp Shells." Biomacromolecules, vol. 4: 12-18, 2003.
Pusateri et al., "Advanced Hemostatic Dressing Development Program: Animal Model Selection Criteria and Results of a Study of Nine Hemostatic Dressings in a Model of Severe Large Venous Hemorrhage and Hepatic Injury in Swine." The Journal of Trauma, vol. 55: 518-526, 2003.
Sandford, Paul A., "Chitosan: Commercial Uses and Potential Applications." Chitin and Chitosan: Proceedings from be 4th International Conference on Chitin and Chitosan, 51-69, 1988.
Sandford et al., "Biomedical Applications of High-Purity Chitosan." Water-Soluble Polymers: Chapter 28: 430-445, 1991.
Sandford, Paul A., "Biomedical Applications of New Forms of Chitin/Chitosan." Chitin Derivatives in Life Science, 12pp., 1992.
Schoof et al., "Control of Pore Structure and Size in Freeze-Dried Collagen Sponges" Journal of Biomedical Material Research, vol. 58: 352-357, 2001.
Siekman, Philip, "A Shrimp Bandage?" Fortune Small Business, pp. 67-68, 2006.
Sondeen et al., "Comparison of 10 Different Hemostatic Dressings in an Aortic Injury." The Journal of Trauma, vol. 54, No. 2: 280-285, 2003.
Wedmore et al., "A Special Report on the Chitosan-based Hemostatic Dressing: Experience in Current Combat Operations." The Journal of Trauma, vol. 60: 655-658, 2006.
Wilson, J.R., "The Army's Greatest Inventions." U.S. Army Materiel Command, pp. 30-37, 2005.
Wu et al., "Development of In Vitro Adhesion Test for Chitosan Bandages." Society for Biomaterials 30th Annual Meeting Transactions, 2005, 1pg.
Database WPI, Week 200873 Thomson Scientific, London GB, AN 2008-M34232, XP002695569 & CN 101138648, Mar. 12, 2008.

* cited by examiner

CHITOSAN FOAM MEDICAL DEVICES AND METHODS

RELATED APPLICATIONS

This application is a divisional of U.S. patent application Ser. No. 13/122,723, filed on Jun. 22, 2011, which claims priority to International PCT patent application serial number PCT/US2009/059726, filed on Oct. 6, 2009, which claims priority to U.S. provisional patent application Ser. No. 61/103,067, filed on Oct. 6, 2008, the contents of each of which are fully incorporated herein by reference.

STATEMENT OF GOVERNMENT INTEREST

This invention was made with Government support under W81XWH-04-1-0841 awarded by the Army Medical Research and Material Command (ARMY/MRMC). The Government has certain rights in the invention.

TECHNICAL FIELD

Embodiments of the present invention relate to methods and devices for controlling bleeding and treating wounds.

BACKGROUND

Excessive blood loss is one of the leading causes of death following severe injury in the battlefield or civilian world. Timely and effective hemorrhage control can not only save victim's lives but also prevent them from post-injury complications and facilitate their wound healing process. Direct pressure at sites of injury by clamping, tourniquet or manual compression in conjunction with medical gauze, has been long used for standard treatment of bleeding wounds on the battlefield. Though many topical hemostatic dressings based on gelatin, collagen and oxidized cellulose have been long used for surgical procedures, they haven't been deployed in the field because of their limited effectiveness in controlling high pressure bleeding. Recently, several new advanced topical hemostats have been developed to treat severe bleeding and deployed for military and civilian emergency use. These include chitosan-based wound dressings.

Chitosan is a derivative of chitin, a naturally occurring biomaterial. There are several advantages by utilizing chitosan as wound dressing material due to its biodegradability, biocompatibility, antibacterial activity, hemostatic activity and bioadhesive property. Chitosan-based wound dressing can be made in a form of powder, film, sheet, patch, sponge, non-woven pad, fabric, mesh, or the like.

Currently there are two physical forms of chitosan-based hemostatic dressings (CELOX™ granules and chitosan bandages) that are commercially available and approved by Food and Drug Administration for temporary hemorrhage control. CELOX™ is lightweight chitosan powder manufactured by MedTrade Products Ltd. The CELOX™ achieves hemostasis by interacting with blood to form a barrier clot at the bleeding site. However, because CELOX™, by nature, has no physical integrity, the powder may be flushed away by ongoing high volume and high pressure bleeding before forming clots. Another disadvantage of CELOX™ is that the manual compression necessary for slowing down blood flow cannot be applied if powder dressing is used alone. Chitosan bandages are a rigid, crystalline chitosan matrix. A combination of its strong adhesive properties and ability to promote clotting makes the bandage effective in controlling severe bleeding when the wounds are open and accessible. However, if the bleeding is from a narrow and deep injury, hemorrhage control by a chitosan bandage may not be effective either because of a difficulty applying the bandage or because of a poor conformity to the injury cavity due to its physical stiffness. Therefore, there is a need to improve the flexibility of chitosan bandages while maintaining or further improving its adhesive properties and hemostatic activity.

BRIEF SUMMARY OF EMBODIMENTS OF THE INVENTION

It is the objective of the present invention to provide a new bioadhesive solid foam wound dressing useful for hemorrhage control and wound repair, as well as methods for making such a wound dressing.

In one aspect the invention provides a superporous matrix in a form of solid foam. In an embodiment of this aspect of the invention, the solid foam is a chitosan-based foam. The resulting foam is mechanically flexible without compromised physical integrity, is adhesive when in contact with physiological fluid or moisture, and is medically useful for hemorrhage control and/or to promote wound healing.

In another aspect, the invention provides a method of making a solid foam wound dressing. In one embodiment of this aspect the method comprises aerating an aqueous chitosan solution comprising at least one protic acid and at least one surface active ingredient to form an aqueous foam, freezing the aqueous foam, dehydrating the aqueous foam to form a solid foam. Embodiments of this aspect may further comprise compressing the solid foam to form a compressed, flexible, solid foam wound dressing. Embodiments of this aspect may further include imprinting a pattern or texture on the surface of the compressed foam to retain a microporous matrix substantially on the surface of the compressed foam.

In another aspect, the invention provides a method of treating a wound. In one embodiment of this aspect the method comprises applying a solid foam wound dressing according to the invention to a wound.

BRIEF DESCRIPTION OF THE FIGURES

Embodiments of the present invention will be readily understood by the following detailed description in conjunction with the accompanying figures.

DETAILED DESCRIPTION OF EMBODIMENTS OF THE INVENTION

Figure 1:
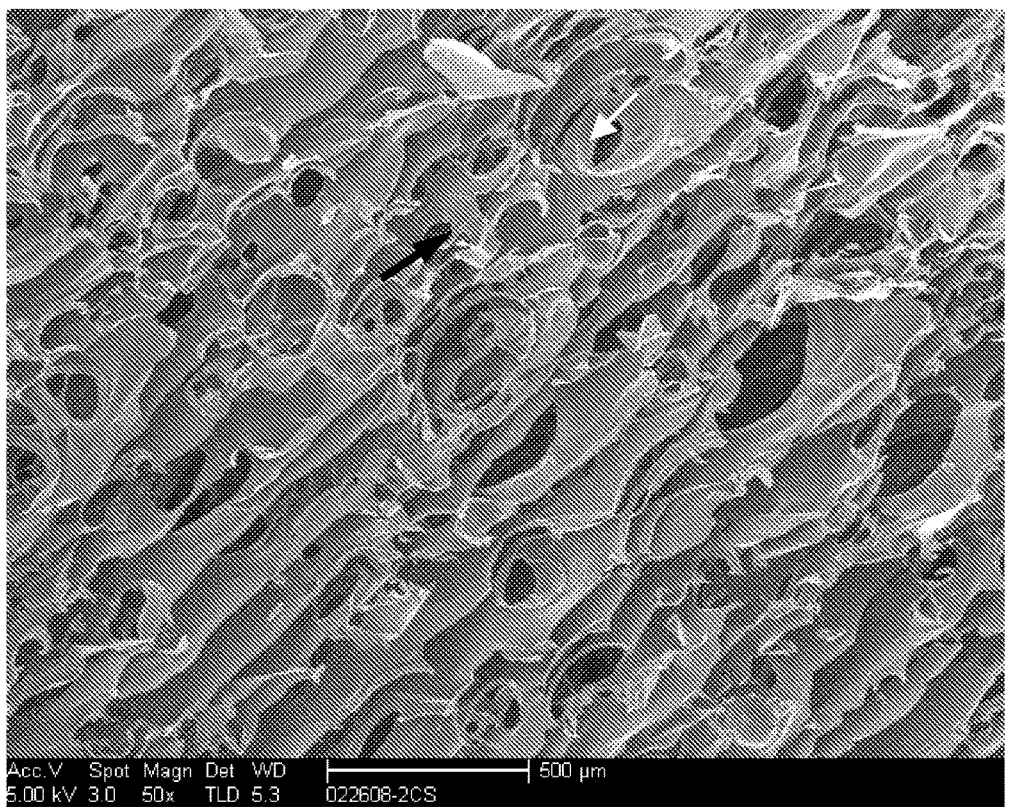
FIG. 1. A scanning electron micrograph at 500× of cross-section of chitosan foam produced in accordance with the present invention.

In the following detailed description, reference is made to embodiments in which the invention may be practiced. It is to be understood that other embodiments may be utilized and structural or logical changes may be made without departing from the scope of the present invention. Therefore, the following detailed description is not to be taken in a limiting sense, and the scope of embodiments in accordance with the present invention is defined by the appended claims and their equivalents.

Various operations may be described as multiple discrete steps in turn, in a manner that may be helpful in understanding embodiments of the present invention; however, the order of description should not be construed to imply that these operations are order dependent.

The description may use the phrases "in an embodiment," or "in embodiments," which may each refer to one or more of the same or different embodiments. Furthermore, the terms "comprising," "including," "having," and the like, as used with respect to embodiments of the present invention, are synonymous.

In various embodiments of the invention, methods and devices for treating wounds are provided. Although certain embodiments have been described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

In one aspect the invention provides a solid foam wound dressing to control severe bleeding, not only in open and easily accessible injured areas but also at narrow and deep wound cavities where an application of current commercially available wound dressing may be limited. Embodiments of this aspect of the present invention include a solid foam wound dressing that is mechanically flexible without compromised physical integrity, capable of interacting with body fluid, having conformity with live tissues, resistant to dissolution, is adhesive when in contact with physiological fluid or moisture, and is medically useful for hemorrhage control and/or to promote wound healing.

Embodiments of this aspect of the invention include a hydrophilic polymer-based foam wound dressing. In some embodiments the hydrophobic polymer is a polysaccharide. The term polysaccharide is intended to include, but is not limited to, chitin, chitosan, starch, cellulose, dextran, alginate, hyaluronate, guar gum, xanthan gum, carrageenan, and their derivatives. In a preferred embodiment, the polysaccharide is chitosan. The term "chitosan" generally refers to a deacetylated derivative of chitin. In various embodiments, the present invention may include one or more derivatives of chitosan. In embodiments of this aspect the wound dressing may further comprise at least one protic acid and/or at least one surface-active agent.

In embodiments of this aspect of the present invention the solid foam comprises lamella and/or open-cell pore structures in which the pores are substantially uniformly distributed and interconnected within the foam. In some embodiments, the solid foam may further comprise microporous imprints on the surfaces of the foam. Thereby providing a solid foam having significantly high surface areas on the surfaces, as well as inside the foam.

Embodiments of this aspect of the present invention may provide one or more advantages over current wound dressings. For example, the solid foam is soft and flexible and can be bent, twisted, folded and rolled; lacks of stiff crust layer on the top surface; comprises a uniform porous structures from bottom to top as well as side to side; has large surface areas; is applicable to narrow-entry and deep wound cavities; quickly interacts with body fluid to form adhesive layer and clot bleeding site; can conform to irregular wound surfaces and cavities, capable of controlling high volume and high pressure bleeding rapidly and effectively; can seal bleeding site and prevent rebleeding; is easy to remove; has enhanced infection protection when surface-active ingredient has inherent antimicrobial properties in addition to foaming ability; and can facilitate wound healing by allowing cells to penetrate and grow through the porous matrix.

In another aspect, the invention provides a method of making a wound dressing. In one embodiment of this aspect the method comprises aerating an aqueous solution comprising a polysaccharide and at least one protic acid and at least one surface active ingredient to form an aqueous foam, freezing the foam, and dehydrating the aqueous foam to form a solid foam. Embodiments of this aspect may further comprise compressing the solid foam to form a compressed, flexible, solid foam wound dressing. Embodiments of this aspect may further include imprinting a pattern or texture on the surface of the compressed foam to retain a microporous matrix substantially on the surface of the compressed foam. In preferred embodiments, the aqueous foam is a chitosan-based foam. The ability to form a solid foam from an aqueous solution is related to the apparent density of the aqueous foam after formation. The lower aqueous foam density, the better solid-foaming ability of the aqueous solution.

In various embodiments, the aqueous foam may be formed by introducing gas bubbles into the aqueous solution through mixing, beating, agitating, aerating, whipping, injecting or other mechanical actions. For such embodiments, the gas may include, but not limited to, air, nitrogen, helium, hydrogen, argon, carbon dioxide or other inert gas. Severity of mechanical actions such as mixing time, speed and temperature may be adjusted depending on foam density and the foam stability desirable for the process, and the softness, flexibility and adhesiveness of final product desirable for medical treatment.

In embodiments according to this aspect of the invention, dehydrating the aqueous foam may include, but not limited to, freeze-drying or lyophilization or other methods known in the art. In embodiments of this aspect, the aqueous foam may be solidified before the gas bubbles trapped in the foam collapse or coalesce. In embodiments of this aspect, the freezing temperature may be controlled in such a way that lamella ice crystals are formed and the trapped gas bubbles are uniformly distributed in the frozen foam before drying. In various embodiments, the freeze temperature may be in the range 0° C. to −200° C., or in the range −10° C. to −80° C. Once the foam is frozen, water and acid in the foam may be removed though sublimation and desorption after a freeze-drying cycle (lyophilization). The final solid foam may be sponge-like and have both lamella and/or open-cell pore structures.

Embodiments of this aspect of the invention may include freezing the foam at a reduced pressure to further expand the gas bubbles trapped in the aqueous foam, prior to a collapse and/or coalescence. In embodiments of this aspect, the reduced pressure environment may be maintained until the expanded gas bubbles are substantially frozen. In such embodiments, the reduced pressure environment may be in the range from 100 mTorr to 750 Torr depending on the freezing temperature, and the desired softness, flexibility and adhesiveness of the final product.

In accordance with various embodiments, the aqueous foam can be made to conform to a desirable shape by transferring the aqueous foam to a heat-conducting container, such as aluminum mold, prior to dehydrating the aqueous foam.

In embodiments of this aspect of the invention, the solid foam may be compressed, for example, between two flat heated platens or rollers under pressure. The solid foam may be compressed to the thickness from 1 to 30 times thinner than uncompressed foam, depending on the density of the uncompressed foam. Preferably, the solid foam may be compressed 2 to 20 times thinner compared to the thickness of uncompressed foam.

In embodiments of this aspect of the invention, the solid foam may be further imprinted with patterns or textures during or after the compression of the solid foam in order to improve coherent strength and flexibility, prevent rapid dissolution and enhance adhesiveness while substantially preserving unique microporous structures on the surfaces. Such imprinting can be achieved by using platens or rollers having patterns or textures or by using soft substrates with patterns or textures loaded between the platens or rollers during compression of the foam. In such embodiments, the temperature of the platens and rollers, with or without the soft substrates, may be controlled at a range from 40° C. to 100° C., preferably from 50° C. to 80° C., depending on the mass of the foam, compression speed and the desirable thickness of the densified matrix.

In an embodiment of the present invention, the soft substrates may comprise a polymeric sheet, mat, and mesh, or knitted or woven fabric having patterns or textures on the surfaces. Preferred soft substrate may include, but not limited to, twill fabrics that have distinct diagonal wale weaving pattern as a result of passing the weft threads over one warp thread and then under two or more warp threads, and may be soft but firm enough to able to densify the solid foam under heating and pressure conditions to form a compressed foam with imprinted surfaces. Compressed foam having imprinted surfaces may comprise a combination of high density and low density matrices as a result of the soft and patterned twill fabric.

In embodiments of the invention, the twill fabric may be 1/2 twill, 2/1 twill, 2/2 twill, 2/1 herringbone twill, 2/2 herringbone twill, 2/1 diamond twill or 2/2 diamond twill, 3/1 twill, 3/2 twill, 4/1 twill, 4/2 twill, 5/1 twill, 5/2 twill, or the like. Preferred twill fabric may include, but not limited to, 2/1 twill, 2/2 twill, 3/1 twill.

In embodiments of the invention, the twill fabric may be made from lint-free synthetic and natural polymers materials. It is preferable the materials are medically acceptable fabrics.

In embodiments of the invention, the soft substrates for the compression in the present invention may have internal heating wires connected to external temperature controller so that platens or rollers are not needed to be heated separately.

In embodiments of the present invention, the concentration of chitosan in the aqueous solution may be in the range from 0.1% to 20% by weight, or in the range of 0.5% to 10% by weight, depending on the molecular weight of the chitosan, foam density and stability desirable for the process, and the softness, flexibility and adhesiveness of final product desirable for medical treatment.

In embodiments of the present invention, the molecular weight of chitosan used in the aqueous solution may be varied from 1 k Dalton to 2000 k Dalton, or from 10 k to 1000 k Dalton, depending on the foam density and stability desirable for the process, and the softness, flexibility and adhesiveness of final product desirable for medical treatment.

In embodiments of the present invention, the protic acid used in the aqueous solution may be a proton donor acid that facilitates dissolving chitosan and stabilizes foam formed during the process. For example, the acid may include, but not limit to, formic acid, acetic acid, propionic acid, lactic acid, succinic acid, glutamic acid, tartaric acid, citric acid, hydrochloric acid, nitric acid, phosphoric acid, and the like. The concentration of acid in the aqueous solution may be in the range from 0.01% to 10% by weight, or from 0.1% to 5% by weight, depending on the stability of foam during the process, and the softness, flexibility and adhesiveness of final product desirable for medical treatment.

In various embodiments, the surface-active agent to aid foam formation and stabilize the foam during the process may be an anionic surface-active agent, cationic surface-active agent, non-ionic surface-active agent, or amphoteric surface-active agent. For example, the anionic surface-active agent may include, but not limit to, sodium or ammonium dodecyl sulfate or caboxylate or phosphate, sodium laureth sulfate, alky benzene sulfonates, sodium carboxyl methylcellulose, sodium stearate, fatty acid sodium salts, phosphatidic acid salt or the like. The cationic surface-active agent may include, but not limit to, fatty amine halides, cetyl trimethylammonium halides, cetylpyrindium halides, benzalkonium halides, benzethonium halides, polyethoxylated tallow amine, or the like. The non-ionic surface active agents may include, but not limit to, methylcellulose, hydroxylethyl cellulose, hydroxyl methypropylcellulose, alky poly(ethylene oxide), octyl glucoside, decyl maltoside, cetyl alcohol, oleyl alcohol, pluronics, tween 20, tween 60, tween 80, or the like. The amphoteric surface-active agents may include, but not limited to, gelatin, white egg, dodecyl betaine, lysozyme, plant proteins, serum albumins, blood plasma, dodecyldimethylamine oxide, cocamidopropyl betaine, coco ampho glycinate, or the like. Preferred surface-active agent for the aqueous solution is water and/or acid soluble cationic, nonionic and amphoteric agents, preferably quaternary ammonium based cationic surface-active agents functioning as both a foaming agent and an antimicrobial and/or antiviral agent, e.g. benzethonium halides, cetyl trimethylammonium halides and the like, can be used for the aqueous solution. The amount of surface-active agent may be varied from 0.001% to 50% by weight, or from 0.01% to 25% by weight, depending on the type of surface-active agent, foam density and stability desirable for the process, and the softness, flexibility and adhesiveness of final product desirable for medical treatment.

In accordance with various embodiments, plasticizers may be optionally used to further improve mechanical and physical properties of the foam. The plasticizers in the aqueous solution may include, but not limit to, glycerol, sorbitol, Tween 60, Tween 80, polyglycol and its derivatives, and the like.

In another aspect, the invention provides a method of treating a wound. In one embodiment of this aspect the method comprises applying a solid foam wound dressing as disclosed herein.

In accordance with various embodiments of the present invention, the wound dressings may help control severe bleeding, not only in open and easily accessible injured areas but also at narrow and deep wound cavities where an application of current commercially available chitosan wound dressing are limited. The new dressing of the present invention has been tested for hemorrhage control in a lethal femoral artery injury animal model. The results shown below demonstrate that the new dressing is very effective at stopping severe bleeding.

Embodiments of the present invention may impart cost savings over prior art methods for producing foam wound dressings. For example, an expansion of gas bubbles trapped in the aqueous foam via reducing pressure before or during freezing in the freeze-drying process may reduce the amount of foaming agent used while achieving the same or even better physical properties. The formation of aqueous foam with high surface area may be favorable for drying during freeze-drying process. Ease of cutting or slicing a solid chitosan-based foam to a desired shape and size of dressing sheet compared to prior chitosan-based structures, which are difficult to cut or slice due to non-uniform crystal structures, may also provide an opportunity to increase the scale of single loading during freeze drying process, thus reducing manufacturing cost.

EXAMPLES

Example 1

Preparation of a Chitosan Foam Formed with Air Bubbles.

A 2% (w/w) chitosan aqueous solution was prepared by dissolving chitosan in acetic acid solutions (2% w/w) in a plastic bottle. The bottle was placed on a roller and rolled until the chitosan was completely dissolved. 900 g of the chitosan solution and 9 gram of benzalkonium chloride solution (2% w/w) as surface-active agent were added to a mixing bowl. The solution was mixed with a mixer (KitchenAid) equipped with a whipping wire to introduce air bubbles to form the foam. The apparent density of the foam was 0.67 g/cm$^3$, determined by weighing 1L of the foam and calculated.

Figure 2:
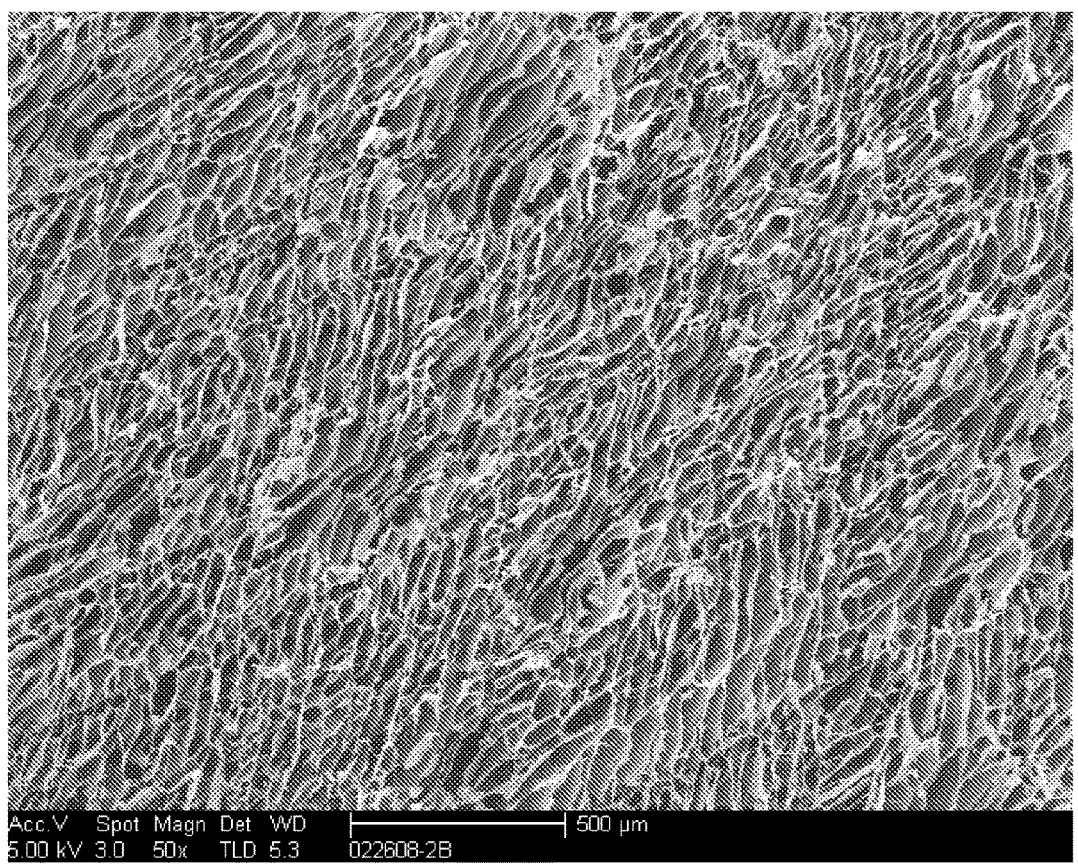
FIG. 2. A scanning electron micrograph at 500× of base surface of chitosan foam produced in accordance with the present invention.
Figure 3:
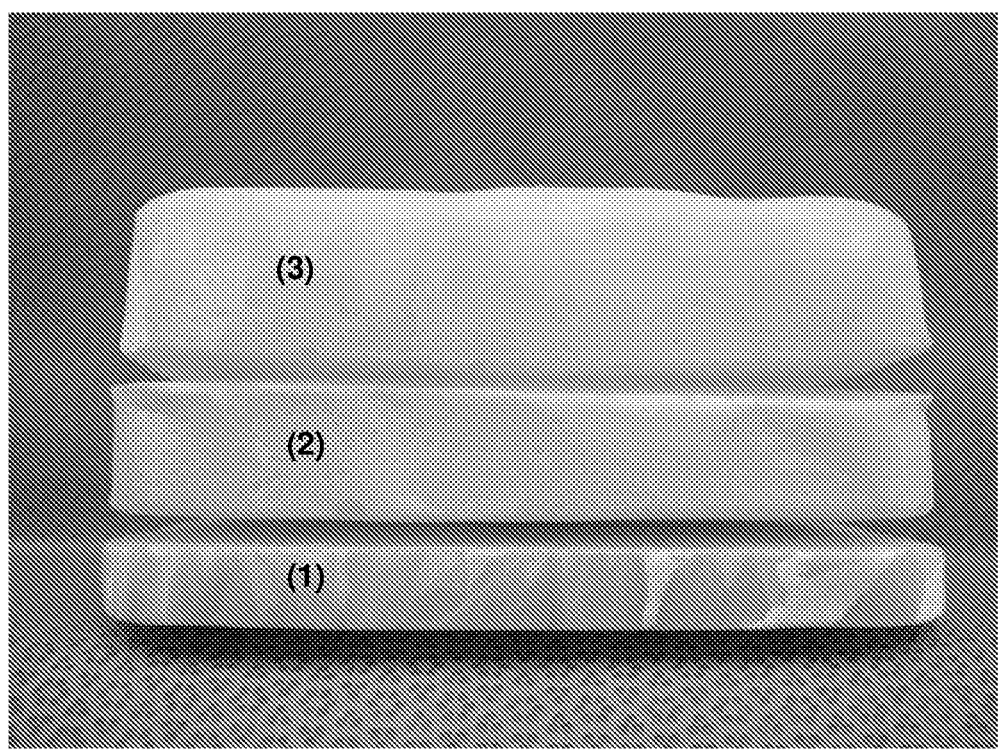
FIG. 3. A photograph of three chitosan foams produced in accordance with the present invention (1) freeze-dried chitosan sponge produced in the absence of surface-active agent (foam density: 0.0370 g/cm$^3$) (2) freeze-dried chitosan foam produced at normal atmosphere during freezing phase (foam density: 0.0211 g/cm$^3$) (3) freeze-dried chitosan foam produced at a reduced pressure (foam density: 0.0124 g/cm$^3$)

FIGS. 1 and 2 show that open-cell pores ranging from few micrometers to over hundreds micrometers randomly but substantially uniformly distributed on the surface of the foam matrix and on each individual lamella layer of the chitosan. The open-cell pores also enabled all lamella pores interconnect cross whole chitosan foam matrix.

Example 2

Preparation of a Chitosan Foam Formed with Carbon Dioxide Bubbles.

A chitosan aqueous solution was prepared by the same procedure described in Example 1 except 40 g of grounded dried ice was added into chitosan aqueous solution before agitation. Foam with a density of 0.69 g/cm$^3$ was obtained.

Example 3

Effects of Chitosan Concentration on Chitosan Foam Formation.

Figure 4:
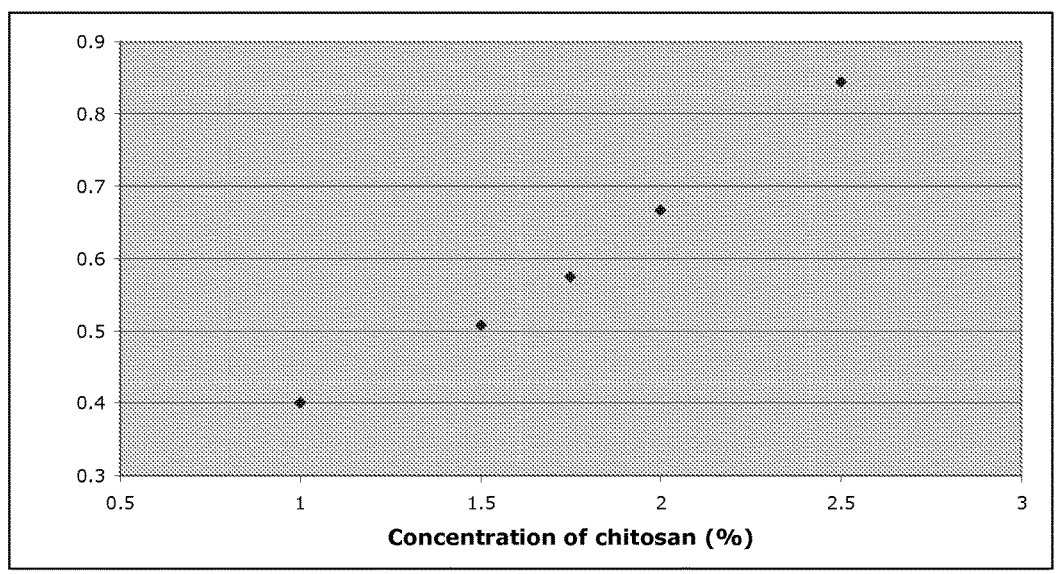
FIG. 4. Effect of chitosan concentration on the density of chitosan aqueous foam in accordance with the present invention.

A chitosan aqueous solution was prepared by the same procedure described in Example 1 except the chitosan concentration in the chitosan solution was varied. A series of chitosan foams with different foam densities were obtained as shown in FIG. 4.

Example 4

Effects of Mechanical Action on Chitosan Foam Formation.

Figure 5:
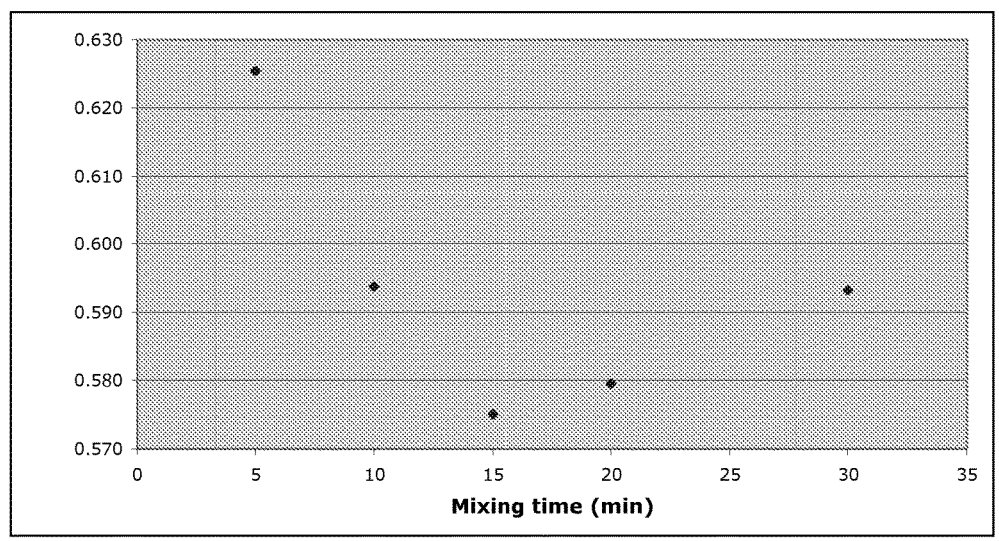
FIG. 5. Effect of mixing time in the preparation of chitosan aqueous foam (1.75% w/w) in accordance with the present invention.

A chitosan aqueous solution was prepared by the same procedure described in Example 1 except the mixing time was varied. A series of chitosan foams with different densities were obtained as shown on FIG. 5.

Example 5

Effects of the Amount of Surface-Active Agent on Chitosan Foam Formation.

Figure 6:
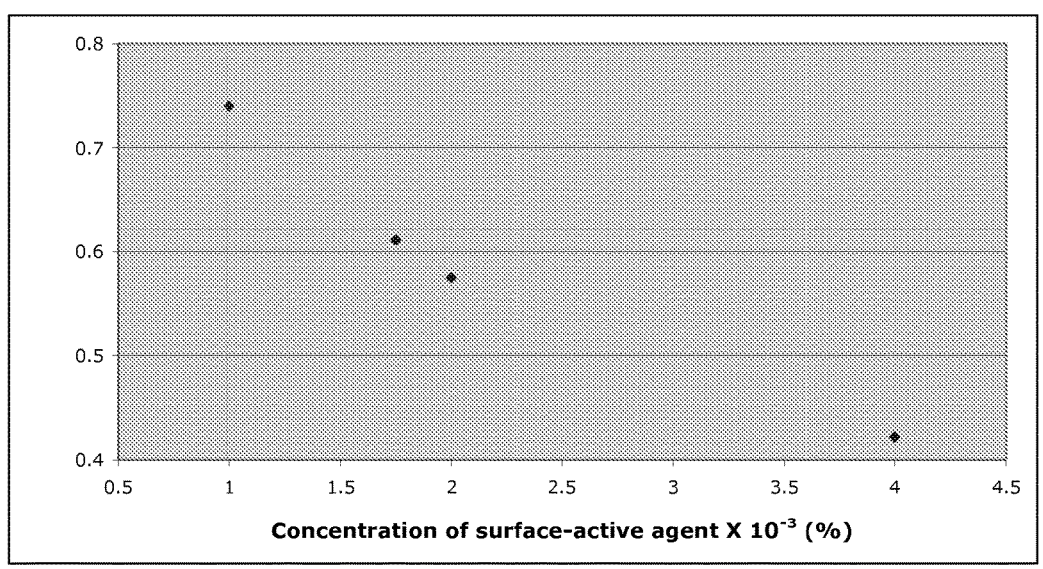
FIG. 6. Effect of cationic surface-active agent on the density of chitosan aqueous foam (1.75% w/w) in accordance with the present invention.

A chitosan aqueous solution was prepared by the same procedure described in Example 1 except the amount of benzalkonium chloride was varied. A series of chitosan foams with different densities were obtained as shown on FIG. 6.

Example 6

Use of an Anionic Surface-Active Agent as a Foaming Agent for Chitosan Foam Formation.

A chitosan aqueous solution was prepared by the same procedure described in Example 1 except benzalkonium chloride was replaced with sodium laury sulfate. A foam with an apparent density of 0.68 g/cm3 was obtained.

Example 7

Preparation of a Chitosan Solid Foam Wound Dressing from Aqueous Foam Through Freeze-Drying.

A 4"×4" aluminum mold was filled the chitosan foam prepared in Example 1. The mold was immediately placed on a pre-cooled freeze dryer shelf and maintained at −40° C. for 3 hours. After complete freezing, the frozen chitosan foam was dried through sublimation and desorption with a full freeze-drying cycle. The final freeze-dried solid foam is soft and flexible. The density of the solid foam was 0.0211 g/cm3. The freeze dried foam was pressed into a thickness of about 1.2 mm on a MTS 858 Mini Bionix II mechanical tester mounted with two flat 6"×6" heated platens. The pressed foam was conditioned in an oven at 80° C. for 15 minutes and sealed in a foil pouch. The chitosan foam was sterilized using gamma irradiation before wound treatment.

Example 8

Preparation of a Chitosan Solid Foam Wound Dressing from Aqueous Foam Frozen at a Reduced Pressure.

An aluminum mold was filled with the chitosan foam prepared in Example 1. The mold was placed on a freezer dryer shelf pre-cooled to −40° C. and immediately the vacuum in the freeze dryer were pulled down to 400 mBar. The shelf temperature was maintained at −40° C. for 3 hours. After complete freezing, the frozen chitosan foam was dried through sublimation and desorption with a full freeze-drying cycle. The final freeze-dried solid foam is softer and more flexible as compared to the solid foam prepared in Example 7. The density of the solid foam is 0.0124 g/cm3. The freeze dried foam was pressed into a thickness of about 1.2 mm on a MTS 858 Mini Bionix II mechanical tester mounted with two flat 6"×6" heated platens. The pressed foam was conditioned in an oven at 80° C. for 15 minutes and sealed in a foil pouch. The chitosan foam was sterilized using gamma irradiation before wound treatment.

Example 9

Preparation of Chitosan Compressed Foam Wound Dressing with Imprinted Surfaces.

The uncompressed freeze dried chitosan foam prepared in Example 8 was pressed between two sheets of lint free 2/1 twill fabrics into a thickness of about 1.2 mm on a MTS 858 Mini Bionix II mechanical tester mounted with two flat 6"×6" heated platens. The final compressed foam with imprinted surfaces had the same distinct patterns as the twill fabric used for the pressing. It is more flexible as compared to the pressed foam with flat and hard surfaces prepared in Example 8 and behaved as a fabric-like dressing. The compressed and imprinted foam dressing was conditioned in an oven at 80° C. for 15 minutes and sealed in a foil pouch. The chitosan foam dressing was sterilized using gamma irradiation before for wound treatment.

Example 10

Hemostatic Testing of Bioadhesive Chitosan Foam in Femoral Artery Injury.

Domestic swine were used for the hemostatic test. An approximate 10 cm incision was made over the groin through the skin and subcutaneous tissues. The thin adductor muscle that directly overlies the femoral canal was excised. At least 5 cm of left femoral artery was isolated (the overlying muscle was removed) and the collateral branches were ligated. The vessel was bathed with a few milliliters of Lidocaine to relax the vasospasm and dilate the artery. A stabilization period of 10-minutes was allowed. To create the injury, the proximal and distal ends of the femoral artery were clamped and an arteriotomy was made on the anterior portion of the femoral artery using a 6.0 mm vascular punch. Caution was taken to avoid the complete transection and retraction of the vessel.

The vessel clamps were released and free bleeding was allowed for 45 seconds. Blood was allowed to accumulate in the wound cavity. Blood spilling out of the cavity was suctioned into canisters. Mean arterial pressure (MAP) dropped to below 40 mmHg. A strip of sterilized chitosan compressed foam (2.8"×14", 5 grams) was then applied to the wound through a pool of blood. While the foam was held down, two pieces of laparotomy gauze were placed over it and compressed for 3 minutes. Hemostasis was checked after compression time. Success was determined when the dressing achieves 30 minutes of hemostasis. Application of the chitosan foams showed that the severe bleeding was stopped and the hemostasis maintained over 30 minutes before testing article was removed. The MAP went back to normal range (>60 mmHg).

What is claimed is:

1. A method of making a solid foam wound dressing, consisting essentially of:
   (I) introducing gas bubbles into an aqueous solution to form an aqueous foam with uniformly distributed gas bubbles therein, wherein the aqueous solution comprises chitosan, at least one protic acid, and at least one surface active agent;
   (II) freezing the aqueous foam prepared in step (I) to form a frozen foam at a pressure of between about 100 mTorr to about 750 Torr before the gas bubbles collapse or coalesce and to expand the gas bubbles in the aqueous foam; and
   (III) dehydrating the frozen foam to form a solid foam with a uniform structure from bottom to top as well as from side to side,
   wherein step (II) occurs immediately after step (I).

2. The method of claim 1, wherein said dehydrating the frozen foam comprises freeze drying the frozen foam.

3. The method of claim 1, further comprising compressing the solid foam.

4. The method of claim 3, further comprising imprinting the compressed solid foam with pattern or texture to provide a microporous surface.

5. The method of claim 4, further comprising imprinting the compressed solid foam with soft substrates having a pattern or texture.

6. The method of claim 1, wherein the protic acid is a hydrogen donator acid.

7. The method of claim 6, wherein the hydrogen donator acid is selected from the group consisting of formic acid, acetic acid, propionic acid, lactic acid, succinic acid, glutamic acid, tartaric, citric acid, hydrochloric acid, nitric and, and phosphoric acid.

8. The method of claim 1, wherein the surface-active agent is anionic, cationic, non-ionic, or amphoteric.

9. The method of claim 8, wherein the cationic surface-active agent is selected from the group consisting of fatty amine halides, cetyl trimethylammonium halides, cetylpyrindium halides, benzalkonium halides, benzethonium halides, and polyethoxylated tallow amine.

10. The method of claim 1, wherein the surface-active agent is antimicrobial and antiviral.

11. The method of claim 1, wherein the gas is selected from the group consisting of air, nitrogen, helium, hydrogen, argon, and carbon dioxide.

12. The method of claim 1, wherein the gas bubbles are introduced by mixing, beating, agitating, aerating, whipping, or injecting the gas into the aqueous solution.

13. The method of claim 1, wherein the wound dressing is capable of promoting hemostasis.

14. The method of claim 1, wherein the wound dressing is capable of promoting wound healing.

15. The method of claim 1, wherein the wound dressing is antimicrobial and antiviral.

16. The method of claim 1, wherein the wound dressing is capable of self adhering to wet tissues.

17. The method of claim 1, wherein the solid foam is cationic.

18. The method of claim 1, wherein the aqueous foam has a density of between about 0.40 g/cm$^3$ to about 0.85 g/cm$^3$.

19. The method of claim 1, wherein the wound dressing is uncompressed and has a density of between about 0.01 g/cm$^3$ to about 0.02 g/cm$^3$.

20. A method of making a solid foam wound dressing, consisting essentially of:
   (I) introducing gas bubbles into an aqueous solution to form an aqueous foam, wherein the aqueous solution comprises chitosan, at least one protic acid and at least one surface active agent;
   (II) freezing the aqueous foam prepared in step (I) to form a frozen foam at a pressure of between about 100 mTorr to about 750 Torr before the gas bubbles collapse or coalesce and to expand the gas bubbles in the aqueous foam; and
   (III) dehydrating the frozen foam to form a solid foam, wherein step (II) occurs immediately after step (I).

21. The method of claim 1, wherein said freezing the aqueous foam prepared in step (II) is done at a pressure of about 400 mBar, or about 300 Torr.

22. The method of claim 20, wherein said freezing the aqueous foam prepared in step (II) is done at a pressure of about 400 mBar, or about 300 Torr.

* * * * *